United States Patent
Song et al.

(10) Patent No.: US 10,267,881 B2
(45) Date of Patent: Apr. 23, 2019

(54) MULTI-ECHO PARAMETRIC VARIATION SATURATION (MEPAVARS CEST IMAGING AND OTHER MR IMAGING

(71) Applicant: THE JOHNS HOPKINS UNIVERSITY, Baltimore, MD (US)

(72) Inventors: Xiaolei Song, Baltimore, MD (US); Michael McMahon, Columbia, MD (US)

(73) Assignee: The Johns Hopkins University, Baltimore, MD (US)

(*) Notice: Subject to any disclaimer, the term of this patent is extended or adjusted under 35 U.S.C. 154(b) by 746 days.

(21) Appl. No.: 14/973,897

(22) Filed: Dec. 18, 2015

(65) Prior Publication Data
US 2016/0187445 A1 Jun. 30, 2016

Related U.S. Application Data (60) Provisional application No. 62/093,625, filed on Dec. 18, 2014.

(51) Int. Cl.
| | |
|---|---|
| G01V 3/00 | (2006.01) |
| G01R 33/56 | (2006.01) |
| A61B 5/055 | (2006.01) |
| G01R 33/561 | (2006.01) |
| A61B 5/00 | (2006.01) |

(52) U.S. Cl.
CPC .......... *G01R 33/5605* (2013.01); *A61B 5/055* (2013.01); *G01R 33/5616* (2013.01); *A61B 5/7257* (2013.01); *G01R 33/5601* (2013.01)

(58) Field of Classification Search
USPC .......................................................... 324/309
See application file for complete search history.

(56) References Cited

U.S. PATENT DOCUMENTS

| | | |
|---|---|---|
| 6,963,769 B1 | 11/2005 | Balaban et al. |
| 7,610,077 B2 | 10/2009 | Dixon et al. |
| 7,683,617 B2 | 3/2010 | Van Zijl et al. |
| 8,536,866 B2 | 9/2013 | Van Zijl et al. |
| 2008/0200799 A1 | 8/2008 | Willard et al. |

(Continued)

OTHER PUBLICATIONS

Song, X., et al., "A Multi-echo Length and Offset VARied Saturation (MeLOVARS) Method for Improved CEST Imaging" Magn Reson Med. (2015) vol. 73, No. 2, pp. 488-496.

(Continued)

*Primary Examiner* — Rodney E Fuller
(74) *Attorney, Agent, or Firm* — Johns Hopkins Technology Ventures

(57) ABSTRACT

CEST MR imaging, called Multi-echo Parametric VARiation Saturation (Me-PaVARS) CEST places multiple image readouts in between a series of saturation pulses. The saturation pulse parameters are varied in a designated systematic pattern, which allows the generation of CEST contrast maps by encoding the patterns of signal loss into the images for better discrimination between various CEST imaging agents. The saturation parameter changes include, but are not limited to, saturation amplitude ($B_1$), saturation length ($t_{sat}$), number of pulses, shape of saturation pulses, amplitude of saturation pulses, saturation offset frequency, or a combination of these variations.

20 Claims, 4 Drawing Sheets

(56) References Cited

U.S. PATENT DOCUMENTS

| | | | |
|---|---|---|---|
| 2012/0271159 A1 | 10/2012 | Song et al. | |
| 2013/0147477 A1* | 6/2013 | Singh | G01R 33/28 324/309 |
| 2014/0213887 A1* | 7/2014 | Reddy | G01R 33/5605 600/414 |
| 2016/0139228 A1 | 5/2016 | McMahon et al. | |
| 2018/0164393 A1* | 6/2018 | Ellingson | G01R 33/4804 |

OTHER PUBLICATIONS

McMahon, M., et al., "Quantifying Exchange Rates in Chemical Exchange Saturation Transfer Agents Using the Saturation Time and Saturation Power Dependencies of the Magnetization Transfer Effect on the Magnetic Resonance Imaging Signal (QUEST and QUESP): pH Calibration for Poly-LLysine and a Starburst Dendrimer" Magn Reson Med (2006) vol. 55, pp. 836-847.

* cited by examiner

MULTI-ECHO PARAMETRIC VARIATION SATURATION (MEPAVARS CEST IMAGING AND OTHER MR IMAGING

CROSS REFERENCE TO RELATED APPLICATIONS

This application claims the benefit of U.S. Provisional Patent Application No. 62/093,625 filed Dec. 18, 2014, which is incorporated by reference herein, in its entirety.

GOVERNMENT SUPPORT

This invention was made with government support under R01 EB015031 awarded by the National Institutes of Health. The government has certain rights in the invention.

FIELD OF THE INVENTION

The present invention relates generally to medical imaging. More particularly the present invention relates to CEST magnetic resonance imaging.

BACKGROUND OF THE INVENTION

Chemical Exchange Saturation Transfer (CEST) imaging has been attracting attention due to its unique characteristics: 1) the ability to detect signals from low concentration species based on the highly selective saturation of rapidly exchanging spins and 2) the capability of detecting changes in environmental parameters in vivo including: pH, temperature and ion concentration. There have been a number of pre-clinical and now also clinical applications which involve either the detection of administered or endogenous CEST agents. A theme of many of these studies involves applying CEST imaging to cancer for characterization of tumor vasculature, metabolism, extracellular pH and nanocarrier uptake.

In order to detect CEST contrast, it is common practice to increment the frequency of a saturation pulse across a range of frequencies. The simple and most common method to detect and quantify CEST contrast is by calculating the asymmetry in the magnetization transfer ratio ($MTR_{asym}$) at the frequency of the exchangeable protons ($\Delta\omega$):

$$MTR_{asyn} = \frac{(S(-\Delta\omega) - S(+\Delta\omega))}{S_0}$$

which is the subtraction of the two water signal intensities with saturation pulse at $+\Delta\omega$ and $-\Delta\omega$ with respect to water, $S(+\Delta\omega)$ and $S(-\Delta\omega)$, normalized by the signal without saturation ($S_0$), or by $S(-\Delta\omega)$ to amplify the dynamic range. Tumors and strokes display contrast on $MTR_{asym}$ maps at saturation offsets between 1-3.5 ppm from water, an effect that has been connected to the amide protons of extra soluble peptides/proteins found in brain tumors which resonate around 3.5 ppm from water, or changes in pH and has been termed Amide Proton Transfer (APT). The amount of APT signal produced by brain tumors was shown to correlate with histopathological grade in patients on clinical 3T scanners, and was also shown to be a marker that could differentiate tumor recurrence from radiation necrosis. There are also attempts to monitor tumor response to HIFU and chemotherapy.

Figure 1A:
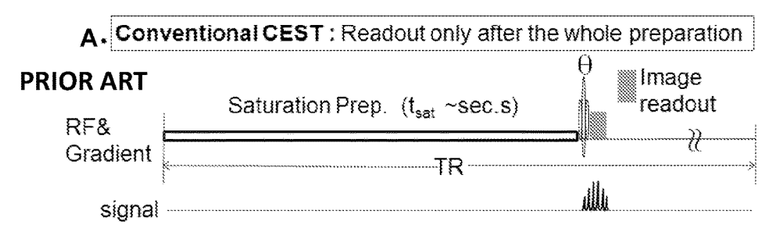
FIG. 1A illustrates a graphical view of an acquisition scheme for a conventional CW CEST experiment.

Although CEST imaging has shown great potential for oncological imaging, there are obstacles towards widespread application, including the low Contrast-Noise-Ratio (CNR) of the images, low specificity, sensitivity to field inhomogeneities, and susceptibility to interference from other sources of contrast. In addition, collection of CEST images can be quite time-consuming. A typical scheme for a CEST pulse sequence is shown in FIG. 1A. Before the water signal readout, a long frequency-selective continuous wave (CW) pulse or pulse train is applied at the resonance frequency of the agent to prepare the magnetization. The Saturation Preparation (Sat. Prep.) pulse(s) is usually on the order of seconds in order to obtain sufficient amplification of signal loss through multiple exchanges of saturated solute protons with water, i.e. low-concentration saturated solute protons are replaced by unsaturated water protons and the new protons are saturated. In addition, for most in vivo data the $MTR_{asym}$ value is not purely CEST contrast, but also includes interference from other sources of water signal loss generated by the saturation pulse, including conventional magnetization transfer contrast (MTC), direct saturation (DS) and relayed Nuclear Overhauser Effect (NOE) transfers. Finally, most endogenous CEST agents resonate between 1-4 ppm from water leading to low specificity for CEST measurements.

Because of the challenges mentioned above, new methods are needed which improve the specificity of CEST measurements or reduce image acquisition times. Recently several acquisition methods have been developed including methods to suppress MTC such as SAFARI, Two-frequency and VDMP and sequences for extracting components of exchange contrast e.g. CERT, Spin-Lock and FLEX. There are also sequences for accelerating CEST data acquisition, such as using RARE or FLASH, CEST-FISP, steady-state methods for fast 3D brain imaging of APT and recently methods based on gradients applied during saturation can push the speed of Z-spectrum collection to single-shot. Gradient-encoded offset methods are intriguing, but currently only have been demonstrated in vitro and might be very challenging in vivo due to inhomogeneous distribution of contrast.

Figure 1B:
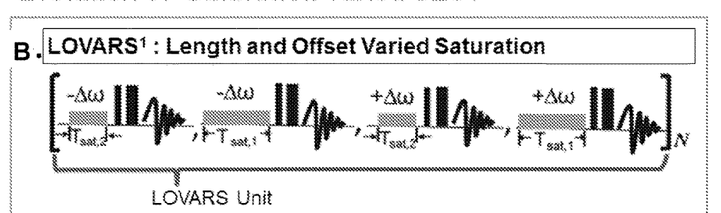
FIG. 1B illustrates a graphical view of an acquisition scheme for LOVARS image acquisition.

One proposed strategy for improving CEST image specificity acquires multiple STw images with different saturation lengths ($t_{sat}$) to add another dimension of information describing the decay in the water signal. Saturation length can also be referred to as duration and time. In simple phantoms (CEST agent in water/PBS), the changes in $MTR_{asym}$ as a function of saturation length ($t_{sat}$) can be used to measure exchange rates ($K_{sw}$), otherwise known as QUEST. In vivo, this Length and Offset VARied Saturation (LOVARS) data can be studied to separate tumor pixels from control brain tissue through the different $t_{sat}$-dependence of $MTR_{asym}$ values. FIG. 1B illustrates a graphical view of an acquisition scheme for LOVARS image acquisition. Based on the knowledge that CEST, DS and MTC behave differently as a function of $t_{sat}$, DS and MTC are predominantly symmetric around the water resonance (CEST is asymmetric), the LOVARS imaging scheme acquires a series of images consisting of N groups of LOVARS' Units (LUs) with 4 images in each LU. The pattern of images collected and the resulting signal is given by the following expression:

$$S_{LOVARS} = [S^1, S^2, S^3, S^4]_{n=1,2,\ldots,N} \qquad [6]$$
$$= [S(-\Delta\omega, T_{sat2}), S(-\Delta\omega, T_{sat,1}),$$

-continued $$S(+\Delta\omega, T_{sat2}), S(+\Delta\omega, T_{sat1})]_{n=1,2,...,N}$$

where $S(-\Delta\omega, T_{sat,2})$ represents the signal for an image with the saturation pulse at frequency=$-\Delta\omega$ and of length=$T_{sat,2}$. Two different saturation offsets are used: 1) $+\Delta\omega$, on resonance with the exchangeable amide protons and 2) $-\Delta\omega$, on the opposite side of water from the exchangeable protons, and two different $t_{sat}$'s, a longer one ($T_{sat,1}$) and a shorter one ($T_{sat,2}$).

Figure 1C:
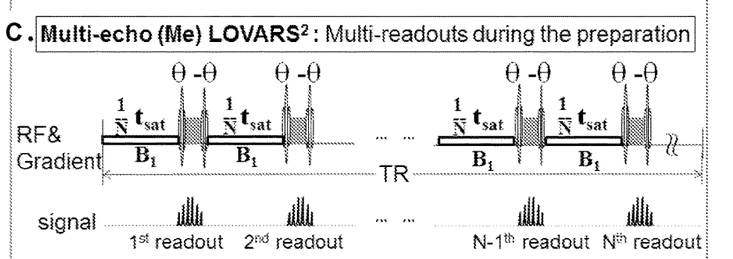
FIG. 1C illustrates a graphical view of an acquisition scheme for MeLOVARS.

This data can discriminate the different levels of interference from MTC, DS and NOE, through collecting $t_{sat}$-dependence information and increase CNR and the specificity of CEST imaging. Unfortunately, it is not practical to acquire images with multiple $t_{sat}$'s and also with multiple saturation offsets (Z-spectra) due to long scan times, although both of them are useful for improving the CEST imaging. FIG. 1C illustrates a graphical view of an acquisition scheme for MeLOVARS. Instead of employing a single long Sat. Prep. module of length $t_{sat}$ (i.e. >1 sec.) before echo readouts, the Me-LOVARS method divides this Sat. Prep. into N=3-10 sub-modules, each with a length of $t_{sat}/N$ (~0.3 sec. −1 sec.), and in between inserts a low flip-angle (FA=$\alpha$) fast gradient echo read-out sequence (here EPI), followed by a flip back pulse (FA=$-\alpha$) for retaining longitudinal magnetization, as illustrated in FIG. 1C. This method could further be improved to allow for better discrimination between various CEST imaging agents.

It would therefore be advantageous to provide an efficient and effective form of CEST magnetic resonance imaging, which enables improvement of the image contrast-to-noise ratio, image specificity and agent quantification in vitro and in vivo.

BRIEF DESCRIPTION OF THE FIGURES

FIGS. 1A-1D illustrate graphical views of image acquisition schemes.

SUMMARY

The foregoing needs are met, to a great extent, by the present invention, wherein in one aspect a method for magnetic resonance imaging of a subject includes using a magnetic resonance imaging machine to generate a series of saturation pulses. The saturation pulses of the series of saturation pulses have varied parameters to generate CEST contrast. There are two or more series of saturation pulses. The method includes obtaining multiple signal readouts between the series of saturation pulses. Additionally, the method includes processing the multiple signal readouts into an image of the subject.

In accordance with an aspect of the present invention, the method for magnetic resonance imaging of the subject further includes using varying parameters such as, but not limited to, saturation amplitude ($B_1$), saturation length ($t_{sat}$), number of pulses, shape of saturation pulses, amplitude of saturation pulse, saturation offset frequency, or a combination of these parameters. The method includes using a low flip-angle gradient-echo readout in the series of saturation pulses. The method can also include using a flip back pulse after the gradient-echo readouts. The method includes varying parameters between series of saturation pulses, such that subsequent series do not have identical parameters.

In accordance with another aspect of the present invention, the method includes creating saturation-transfer contrast patterns that depend on the chemical exchange properties of exchanging protons. The method also includes detecting saturation-contrast patterns in the resultant signal readouts. The method includes processing the multiple signal readouts with methods such as, but not limited to, fast fourier transform (FFT), the general linear model (GLM) or other signal conditioning methods. At least one CEST contrast agent can be delivered to the subject. It can also be used in the cases of tissue endogenous contrast when no agents are administered. Additionally, the method can be executed using a non-transitory computer readable medium.

In accordance with another aspect of the present invention, a system for magnetic resonance imaging of a subject includes a magnetic resonance imaging machine configured to generate a series of saturation pulses, wherein the saturation pulses or the series of saturation pulses have varied parameters to generate CEST contrast, and wherein there are two or more series of saturation pulses. The system also includes a non-transitory computer readable medium programmed for obtaining multiple signal readouts between the series of saturation pulses. The non-transitory computer readable medium is also programmed for processing the multiple signal readouts into an image of the subject.

In accordance with yet another aspect of the present invention, the varied parameters include saturation amplitude ($B_1$), saturation length ($t_{sat}$), number of pulses, shape of saturation pulses, amplitude of saturation pulses, offset frequency of saturation pulses, or a combination of these parameters. The system can include a low flip-angle gradient-echo readout. The magnetic resonance imaging machine is configured for a flip back pulse in between the series of saturation pulses. The varied parameters are varied between series of saturation pulses, such that subsequent series do not have identical parameters. Saturation-transfer contrast patterns depend on the chemical exchange properties of exchanging protons. The non-transitory computer readable medium is programmed for detecting saturation-contrast patterns in the resultant signal readouts. The non-transitory computer readable medium is programmed for processing the multiple signal readouts with at least one selected from a group consisting of fast fourier transform (FFT), the general linear model (GLM) or other signal conditioning methods. A CEST contrast agent is delivered to the subject or monitoring the tissue endogenous contrast without a CEST contrast agent. The non-transitory computer readable medium is loaded onto a computing device in communication with the magnetic resonance imaging machine.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

The present invention provides a novel approach for CEST MR imaging, called Multi-echo Parametric VARiation Saturation (Me-PaVARS) CEST. This method places multiple image readouts in between a series of saturation pulses. The saturation pulse parameters are varied, which allows the generation of CEST contrast maps with patterns of signal loss encoded into the images for better discrimination between various CEST imaging agents, according to the signal loss patterns produced by variation of saturation conditions. The saturation parameter changes include, but are not limited to, saturation amplitude ($B_1$), saturation length ($t_{sat}$), number of pulses, shape of saturation pulses, amplitude of saturation pulses, saturation offset frequency, or a combination of these variations.

The sequence enabling rapid collection of CEST images is based on saturation modules, each consisting of a saturation pulse or series of pulses, a low flip-angle gradient-echo readout and may include a flip back pulse or may not, with at least two modules included in the sequence with the saturation parameters varied between successive modules. Systematically changing the saturation parameters (as mentioned above), creates saturation-transfer contrast patterns, which depend on the chemical exchange properties of exchanging protons allowing detection and discrimination using various pattern-recognition methods. This allows improvement of the image Contrast-to-Noise Ratio, image specificity and agent quantification in vitro and in vivo. The claimed methodology presents specific advantages for determining whether differences in saturation transfer contrast are due to differences in exchange rate or differences in agent concentration.

The conventional CEST-MRI methods are based on offset frequency correction for correcting $B_0$ field inhomogeneity, which suffer from long acquisition times, image distortions due to field inhomogeneities, poor image quality of the contrast maps and different sources of artifacts. The designed MePaVARS sequence of the present invention takes advantage of the unique response of CEST contrast to saturation pulse length, strength (and Offset) and utilizes this and post-processing to create improved contrast maps. The MePaVARS sequence generates new types of CEST contrast maps, which can be less sensitive to distortion by magnetic field inhomogeneity, possess higher CNR, or can describe the buildup of exchange contrast as a function of saturation amplitude and/or length. Saturation amplitude can also be referred to as saturation power or saturation field strength. The MePaVARS sequence also separates CEST contrast from other sources of signal loss such as direct saturation or conventional Magnetic Transfer contrast and separates CEST contrast occurring at different saturation frequencies from each other. Additionally, the MePaVARS sequence shortens the scanning time and increases the contrast-to-noise ratio and efficiently generates specific signal oscillation patterns from the multiple readouts which can improve CEST specificity, such as separation of different species of exchange rate. A methodology according to the present invention can clearly distinguish between the contribution from the exchange rate and the concentration.

Figure 1D:
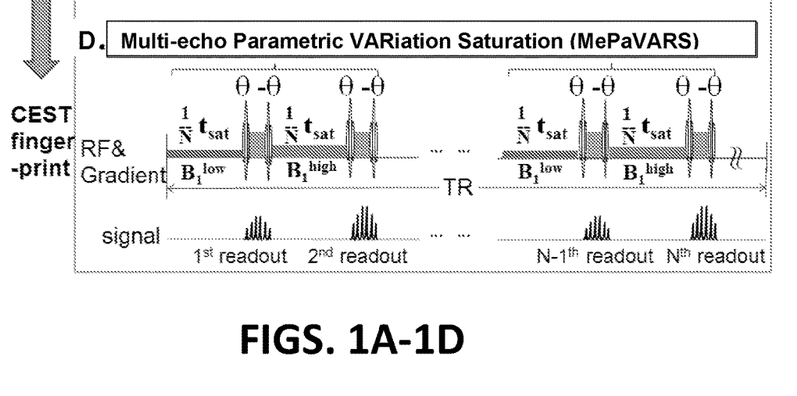
FIG. 1D illustrates a graphical view of an exemplary of the acquisition schemes for Multi-echo Parametric VARiation Saturation (MePaVARS) with the series of signal readouts specifically depending on the CEST contrast of the pixel/voxel, according to an embodiment of the present invention.

The detailed figures and description of these figures included herein displays how the MePaVARS sequence enables efficient encode patterns into the MRI signal based on variations in saturation parameters. FIG. 1D illustrates a graphical view of an acquisition scheme for Multi-echo Parametric VARiation Saturation with the series of signal readouts specifically depending on the CEST contrast of the pixel/voxel, according to an embodiment of the present invention. A sequence enabling rapid collection of CEST images is based on saturation modules, each consisting of a saturation pulse or series of pulses, a low flip-angle gradient-echo readout and may include a flip back pulse or may not, with at least two modules included in the sequence with the saturation parameters varied among the N modules. Multiple image readouts are taken in between the at least two modules, and if more than two modules are used, image readouts are taken in between each of the successive modules.

Figure 2A:
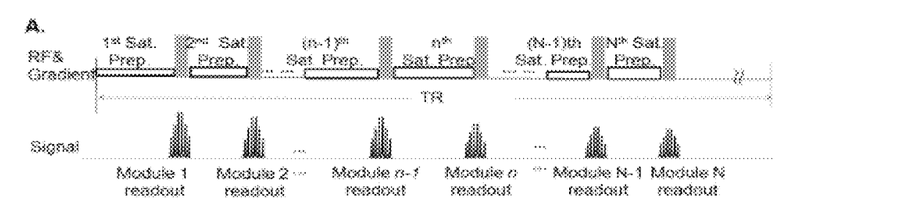
FIGS. 2A and 2B illustrate in further detail a graphical view of an acquisition scheme for Multi-echo Parametric VARiation Saturation with the series of signal readouts specifically depending on the CEST contrast of the pixel/voxel, according to an embodiment of the present invention.
Figure 2B:
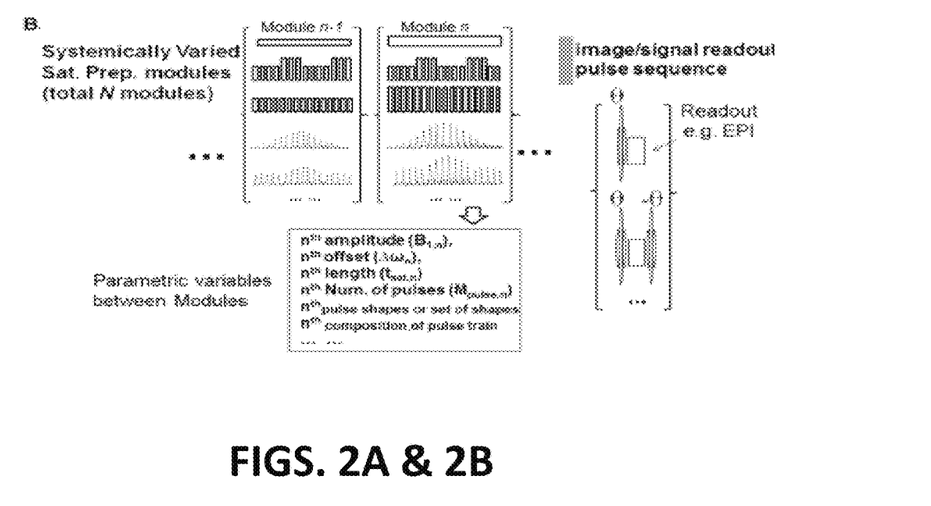

FIGS. 2A and 2B illustrate in further detail a graphical view of an acquisition scheme for Multi-echo Parametric VARiation Saturation for modulating CEST contrast with interleaved image acquisition, according to an embodiment of the present invention. FIG. 2A is an overview of the pulse sequence for MePaVARS, including N multi-parametric Varied saturation preparation (Sat. Prep.) modules, each followed by a signal readout module (in practice N≥2). FIG. 2B further illustrates the different forms that the systematic variations in the saturation prep period of the modules can take, including, but not limited to, changes in saturation amplitude ($B_{1,n}$), changes in offset ($\Delta\omega_n$), changes in length ($t_{sat}$,n), changes in Num. of pulses in a pulse train ($M_{pulse,n}$), changes in the pulse shape(s) or amplitudes of selected pulses within the train etc. The resulting signal readouts in each module will display differences due to the variation in saturation pulse(s) and the build-up of saturation transfer experienced by the spins.

In an exemplary implementation of the method of the present invention, a CEST agent, 5-Amino salicylic acid, featuring an intramolecular-bond shifted hydrogen (IM-SHY)$^3$ offset $\Delta\omega$ of 8.5 ppm was dissolved in PBS (20 mM). Samples at pH values 6.9 and 7.2 in 5 mm NMR tubes were imaged on a Bruker Biospec 17.6 T vertical-bore scanner at 310K, using a 15 mm volume coil as trans/receiver. Fast CEST acquisition was performed using a hybrid MeLO-VARS sequence (FIG. 1C) containing 8 modules with saturation pulses of 0.5 sec. in length with $B_1^{low}$=3.6 uT (Module 1, 3, 5, 7) and $B_1^{high}$=7.2 uT (Module 2,4,6,8), each followed by a single-shot EPI readout. Two regular MeLO-VARS sequences of eight modules with either $B_1$=7.2 uT or $B_1$=3.6 uT were also collected for comparison, with all the other parameters same. The image parameters are: TR/TE=8 s/5.25 ms, EPI module time=11 ms and Matrix Size=64×48. Z-spectra were acquired with the saturation offset incremented 0.3 ppm from −9.9 ppm to −6.9 ppm, and from 6.9 ppm to 9.9 ppm.

Figure 3A:
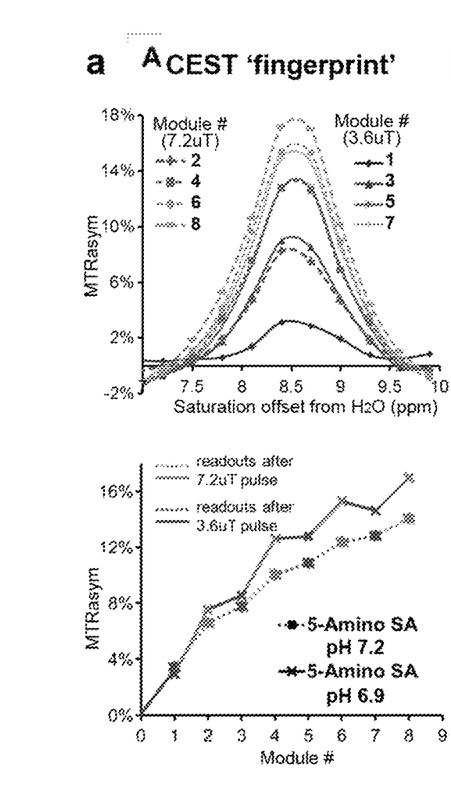
FIGS. 3A-3D illustrate graphical views of data obtained in accordance with the proposed Multi-echo Parametric VARiation Saturation scheme with the series of signal readouts specifically depending on the CEST contrast of the pixel/voxel, according to an embodiment of the present invention.
Figure 3B:
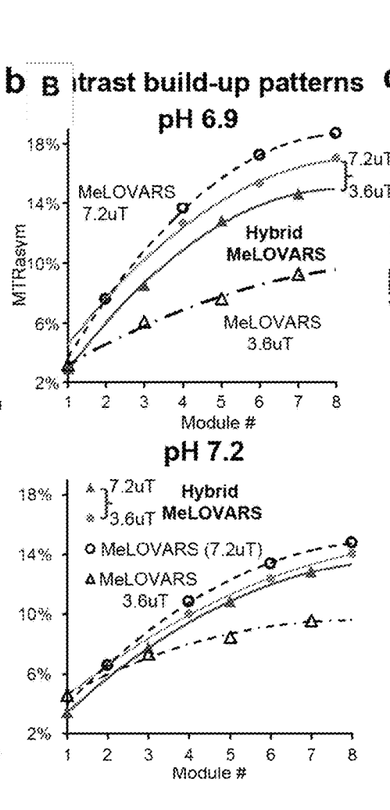
Figure 3C:
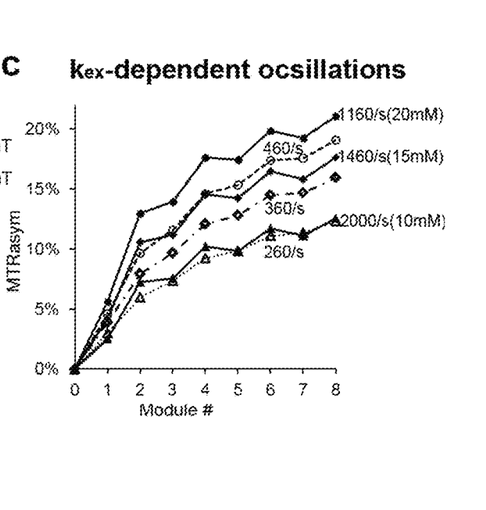

FIGS. 3A-3D illustrate graphical views of data obtained in accordance with the proposed exemplary Multi-echo Parametric VARiation Saturation scheme with the series of signal readouts specifically depending on the CEST contrast of the pixel/voxel, according to an embodiment of the present invention, described above. FIG. 3A shows the 8 CEST $MTR_{asym}$ spectra acquired simultaneously by the hybrid MeLOVARS method for 5-Amino SA of pH=6.9, generating a CEST 'fingerprint' (the upper row), which is also similar morphologically to a real fingerprint. For the frequencies around the peak (8.7 ppm here), the $MTR_{asym}$ build-up pattern based on varied saturation $B_1$ and $t_{sat}$, shows a pattern with larger oscillations for pH 6.9 with a higher exchange rate (~900/s), compared with that for pH 7.2 with a lower $k_{ex}$ (~600/s). FIG. 3B further compared the contrast build-up patterns acquired using MePaVARS, compared with the conventional MeLOVARS with only 7.2 uT or with only 3.6 uT. Based on a 2-pool Bloch-equation simulations, the signal oscillation patterns were generated using MePaVARS for multiple samples with distinct $K_{ex}$ and concentrations. FIG. 3C illustrates a graphical view of samples with higher $K_{ex}$ oscillating more than that with lower $K_{ex}$ (all with concentration of 35 mM), but not dependent on their concentrations. As shown, although their $MTR_{asym}$ values are similar due to contributions from the concentrations (all conc. are 35 mM for three curves of lower $k_{ex}$ values), in MePaVARS build-up curves higher $k_{ex}$ (>500/s) shows additional high-frequency oscillations compared to the more-smoothed build-up patterns similar to previous QUEST/QUESP curves (FIG. 3C).

Figure 3D:
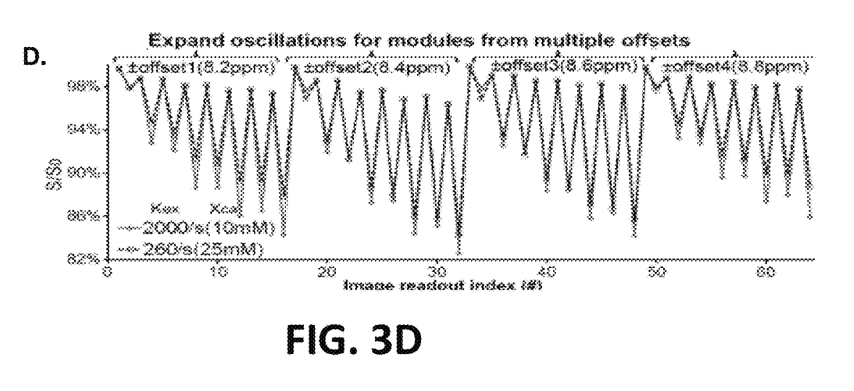

FIG. 3D shows examples of signal patterns generated using MePaVARS which can be organized in multiple ways and analyzed through data mining techniques or conditioned through post-processing procedures such as the fast fourier transform (FFT), the general linear model (GLM), or other signal conditioning methods. In the examples in FIG. 3D, 8 modules were employed, each containing one 0.5 s Continuous Wave (CW) saturation pulse, with the power of this pulse alternating between 3.6 µT and 7.2 µT from module n to module n+1 to display the build-up of saturation contrast for both field strengths as a function of saturation length. The upper left panel displays the $MTR_{asym}$ ($MTR_{asym}=(S(-\Delta\omega)-S(+\Delta\omega))/S_0$) data as a function of frequency for the multiple modules collected on a 25 mM concentration of a CEST agent with $\Delta\omega=8.5$ ppm and $k_{ex}\sim560$ $s^{-1}$, to display the build-up pattern. In order to highlight how the signal patterns might vary with exchange rate and concentration changes, simulations were performed to predict the MePaVARS patterns. As the upper right panel shows, although the $MTR_{asym}$ values are similar, the amplitude of the oscillations seen within the $MTR_{asym}$ (8.6 ppm) curves changes, with higher $k_{ex}$ (>600/s) producing stronger oscillations compared to the smoother curves for slower rates which are more similar to previous QUEST/QUESP data (McMahon et al., 2006, Mag Res Med 55: 836-847. 108). The lower panel displays an alternate way to display this data, plotting instead $S(-\Delta\omega)$ and $S(+\Delta\omega)$ for the four offsets acquired, and also can be used to distinguish differences in the signal patterns.

Overall, the proposed high-throughput method enables fast acquisition of additional information for saturation-transfer contrast build-up based on systematically varying the saturation within one TR of a multi-echo acquisition. This allows improvement of CNR, specificity, sensitivity, and quantitation for in vitro and in vivo CEST, NOE and other magnetization-transfer contrast images.

Based on the idea of varied saturation CEST, a Multi-echo Parametric VARiation Saturation (MePaVARS) method was developed which is a hybrid MeLOVARS method, enabling fast acquisition of multi-parametric saturation weighted images. On phantom data, it allows separation of different pH solutions according to the additional saturation-modulation patterns. This potentially allows separation of $K_{ex}$ contributions to CEST contrast from concentration contributions. It also has potential in vivo for modulating different saturation contrasts and increasing the specificity of CEST imaging.

It should be noted that the pulse sequences, imaging protocols, described herein can be executed with a program (s) fixed on one or more non-transitory computer readable medium. The non-transitory computer readable medium can be loaded onto a computing device, server, imaging device processor, smartphone, tablet, phablet, or any other suitable device known to or conceivable by one of skill in the art. The computing device can be in communication with the magnetic resonance imaging machine. This communication can be wired, wireless, over a network, via a server, via Bluetooth™, or any other suitable means of communication known to or conceivable by one of skill in the art.

It should also be noted that herein the steps of the method described can be carried out using a computer, non-transitory computer readable medium, or alternately a computing device, microprocessor, or other computer type device independent of or incorporated with an imaging or signal collection device. An independent computing device can be networked together with the imaging device either with wires or wirelessly. Indeed, any suitable method of analysis known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A method for magnetic resonance imaging of a subject comprising:
   using a magnetic resonance imaging machine to generate a series of saturation pulses, wherein the saturation pulses or the series of saturation pulses have varied parameters to generate CEST contrast, and wherein there are two or more series of saturation pulses;
   obtaining multiple signal readouts between the series of saturation pulses; and
   processing the multiple signal readouts into an image of the subject.

2. The method for magnetic resonance imaging of the subject of claim 1 further comprising varying parameters chosen from a group consisting of saturation amplitude ($B_1$), saturation length ($t_{sat}$), number of pulses, shape of saturation pulses, amplitude of saturation pulses, offset frequency of saturation pulses, or a combination of these parameters.

3. The method for magnetic resonance imaging of the subject of claim 1 further comprising using a low flip-angle gradient-echo readout.

4. The method for magnetic resonance imaging of the subject of claim 1 further comprising using a flip back pulse in between the series of saturation pulses.

5. The method for magnetic resonance imaging of the subject of claim 1 further comprising varying the parameters between series of saturation pulses, such that subsequent series do not have identical parameters.

6. The method for magnetic resonance imaging of the subject of claim 1 further comprising creating saturation-transfer contrast patterns that depend on the chemical exchange properties of exchanging protons.

7. The method for magnetic resonance imaging of the subject of claim 6 further comprising detecting saturation-contrast patterns in the resultant signal readouts.

8. The method for magnetic resonance imaging of the subject of claim 1 further comprising processing the multiple signal readouts with at least one selected from a group consisting of fast fourier transform (FFT), the general linear model (GLM) or other signal conditioning methods.

9. The method for magnetic resonance imaging of the subject of claim 1 further comprising delivering a CEST contrast agent to the subject or monitoring the tissue endogenous contrast without a CEST contrast agent.

10. The method for magnetic resonance imaging of the subject of claim 1 further comprising using a non-transitory computer readable medium.

11. A system for magnetic resonance imaging of a subject comprising:
   a magnetic resonance imaging machine configured to generate a series of saturation pulses, wherein the saturation pulses or the series of saturation pulses have varied parameters to generate CEST contrast, and wherein there are two or more series of saturation pulses;
   a non-transitory computer readable medium programmed for:
   obtaining multiple signal readouts between the series of saturation pulses; and
   processing the multiple signal readouts into an image of the subject.

12. The system for magnetic resonance imaging of the subject of claim 11 further comprising the varied parameters being chosen from a group consisting of saturation amplitude ($B_1$), saturation length ($t_{sat}$), number of pulses, shape of saturation pulses, amplitude of saturation pulses, offset frequency of saturation pulses, or a combination of these parameters.

13. The system for magnetic resonance imaging of the subject of claim 11 further comprising a low flip-angle gradient-echo readout.

14. The system for magnetic resonance imaging of the subject of claim 11 further comprising the magnetic resonance imaging machine being configured for a flip back pulse in between the series of saturation pulses.

15. The system for magnetic resonance imaging of the subject of claim 11 further comprising the varied parameters being varied between series of saturation pulses, such that subsequent series do not have identical parameters.

16. The system for magnetic resonance imaging of the subject of claim 11 further comprising saturation-transfer contrast patterns that depend on the chemical exchange properties of exchanging protons.

17. The system for magnetic resonance imaging of the subject of claim 16 further comprising the non-transitory computer readable medium being programmed for detecting saturation-contrast patterns in the resultant signal readouts.

18. The system for magnetic resonance imaging of the subject of claim 11 further comprising the non-transitory computer readable medium being programmed for processing the multiple signal readouts with at least one selected from a group consisting of fast fourier transform (FFT), the general linear model (GLM) or other signal conditioning methods.

19. The system for magnetic resonance imaging of the subject of claim 11 further comprising a CEST contrast agent delivered to the subject or monitoring the tissue endogenous contrast without a CEST contrast agent.

20. The system for magnetic resonance imaging of the subject of claim 11 further comprising the non-transitory computer readable medium being loaded onto a computing device in communication with the magnetic resonance imaging machine.

* * * * *